United States Patent [19]
de Luca et al.

[11] 3,935,462
[45] Jan. 27, 1976

[54] WHOLE BODY IMAGING

[75] Inventors: Peter C. de Luca, Medfield; Hugh F. Stoddart, Groton; David Jeffries, Milton, all of Mass.

[73] Assignee: Cleon Corporation, Needham, Mass.

[22] Filed: Mar. 4, 1974

[21] Appl. No.: 447,990

[52] U.S. Cl.................................. 250/369; 250/366
[51] Int. Cl.²........................................... G01T 1/20
[58] Field of Search ............ 250/327, 363, 366, 369

[56] References Cited
UNITED STATES PATENTS
3,509,341   4/1970   Hindel et al. ..................... 250/366
3,777,142   12/1973  Grenier............................. 250/327

*Primary Examiner*—Archie R. Borchelt
*Attorney, Agent, or Firm*—Charles Hieken, Esq.; Jerry Cohen, Esq.

[57] ABSTRACT

A whole body imaging system rapidly forms a quality image of the bony structure, soft tissue or specific organs of a patient who has been injected with a suitable radioactive tracer chemical. A radiation detector head assembly includes a number of detector subassemblies, each having a lead collimator with tapered holes for admitting gamma radiation from a small area of the patient to a scintillation crystal that converts the gamma rays admitted by the collimator into visible or ultraviolet energy pulses. A photomultiplier converts these pulses into electrical pulses. A row of equally spaced detector subassemblies reciprocate within a nonreciprocating lead shield along the long axis of the array over a distance substantially equal to the separation between adjacent ones of the small areas. Associated electronic and electromechanical apparatus control the reciprocating motion and the longitudinal motion of the radiation detector head assembly and process the photodetected signals to produce in a relatively short time a visible image of the radiant energy emanating from the whole body of the patient scanned.

10 Claims, 9 Drawing Figures

WHOLE BODY IMAGING

BACKGROUND OF THE INVENTION

The present invention relates in general to radiant energy imaging and more particularly concerns novel apparatus and techniques for rapidly providing an image of the whole body of a patient who has been injected with a suitable radioactive tracer chemical. The invention is characterized by a number of features that enable a diagnostician to rapidly obtain considerable information about the patient in a relatively short time with safety, with minimal discomfort to the patient and in a form that facilitates greater and repeated examination and processing by a computer or other automatic data processing device.

A useful diagnostic tool for essentially noninvasively diagnosing the condition of a patient is a radiant energy image of the whole body produced by injecting a suitable radioactive tracer chemical into the patient and then scanning the patient to effectively provide a map of the radiation intensity from the patient.

A major problem in obtaining these maps is the length of time for obtaining the radiant energy image of suitable resolution. Prior art approaches typically require longer than twenty minutes to produce radiant energy images of the whole body of a patient. To keep an ill patient still for such a long period is difficult and discomforting to the patient.

One prior art approach is disclosed in U.S. Pat. No. 3,509,341 using a multichannel scanner having a linear array of scintillation crystals comprising radiation detectors. The linear detector array is parallel to the long axis of the patient and reciprocates in a direction normal to the length of the array. After each stroke of the transverse reciprocal motion, typically an amplitude of 45 cm, the whole array indexes a fraction of an inch in the longitudinal direction. This scan-and-step sequence repeats until the sum of the lengthwise increments just equals the separation between the focal points of the array to complete a scan for an area of width corresponding to the transverse scan amplitude, typically 45 cm, and the length of the array; that is, the number of detectors multiplied by the separation between detectors. This approach necessarily limits the size of a single frame or scan-area to an area much smaller than the projected area of an adult patient. Thus, to scan the whole body of an adult, several individual frames are required over a time interval longer than that desired. In the commercially available Dynapix system the patient is moved between successive frames.

Accordingly, it is an important object of this invention to provide an improved radiant energy imaging system that overcomes one or more of the disadvantages enumerated above.

It is another object of the invention to achieve the preceding object with a radiant energy imaging system that may scan the whole body in a relatively short interval.

It is a further object of the invention to achieve one or more of the preceding objects with a system that does not subject a patient to appreciable discomfort or anxiety.

It is a further object of the invention to achieve one or more of the preceding objects with a system that provides great flexibility in terms of information density, the ability to monitor the resultant image and to study the image at any time with or without computer or other automatic data processing apparatus assistance.

It is a further object of the invention to achieve one or more of the preceding objects with equipment that is relatively safe and reliable.

SUMMARY OF THE INVENTION

According to the invention, there is means defining a plurality of spaced radiant energy detectors equally spaced along a curve for providing a corresponding plurality of electrical signals each representative of the radiant energy focused thereon from a corresponding plurality of points on a body, the curve being generally transverse to the length of the body. There is first scan drive means for translating said detectors together along said curve to scan a portion of the body along a similar curve, and second scan means for advancing said plurality of detectors along the length of the body at a rate ordinarily less than the rate of translating the detectors along the curve. Preferably, the curve is a line transverse to the length of the body support, the first means for scanning includes means for reciprocating the detectors together along the line and the second means for scanning includes means for slowly moving the row of detectors along the length of the body while the detectors reciprocate along the line. This scanning system effectively scans a zig-zag pattern of individual focal points along the scanned body of width substantially the same as the separation between adjacent detectors to scan a total area equal to this separation width times the number of detectors along the transverse line multiplied by the longitudinal distance translated by the row of detectors moving from one end of the body to the other. According to another aspect of the invention there is a row of detectors above and a row of detectors below the scanned body and means for moving the two rows of detectors together so that two radiant energy images, usually representing different horizontal planes within the patient, are formed simultaneously.

According to another feature of the invention, there is means for modulating the beam of a cathode ray tube with the multiplexed output signals provided by the individual detector subassemblies so that the on-time of the electron beam corresponds to the density of the radioactivity from the focal point of a detector associated with a corresponding point on the face of the cathode ray tube.

Still another feature of the invention resides in a read-only memory and associated circuitry so that the amplitude of each multiplexed output signal from a respective detector controls the duration of a pulse-width command for off-on modulation of the beam of a CRT to expose a photographic film of known exposure characteristics and thereby record patient density information, effectively converting radiation intensity to exposure time and producing equally discernible density differences in the final photographic image.

Still another feature of the invention resides in means for injecting an electronic gray scale signal into the signal processing and display system so that a gray scale, or series of known exposure values, may be introduced upon the photographic film to assist the user in achieving optimum exposure of the film, or optimum processing of the film subsequent to exposure and to relate the density at any point of the exposed film to the radioactivity density in the corresponding place in the patient.

Numerous other features, objects and advantages of the invention will become apparent from the following specification when read in connection with the accompanying drawing in which:

DETAILED DESCRIPTION OF PREFERRED EMBODIMENTS

Figure 1:
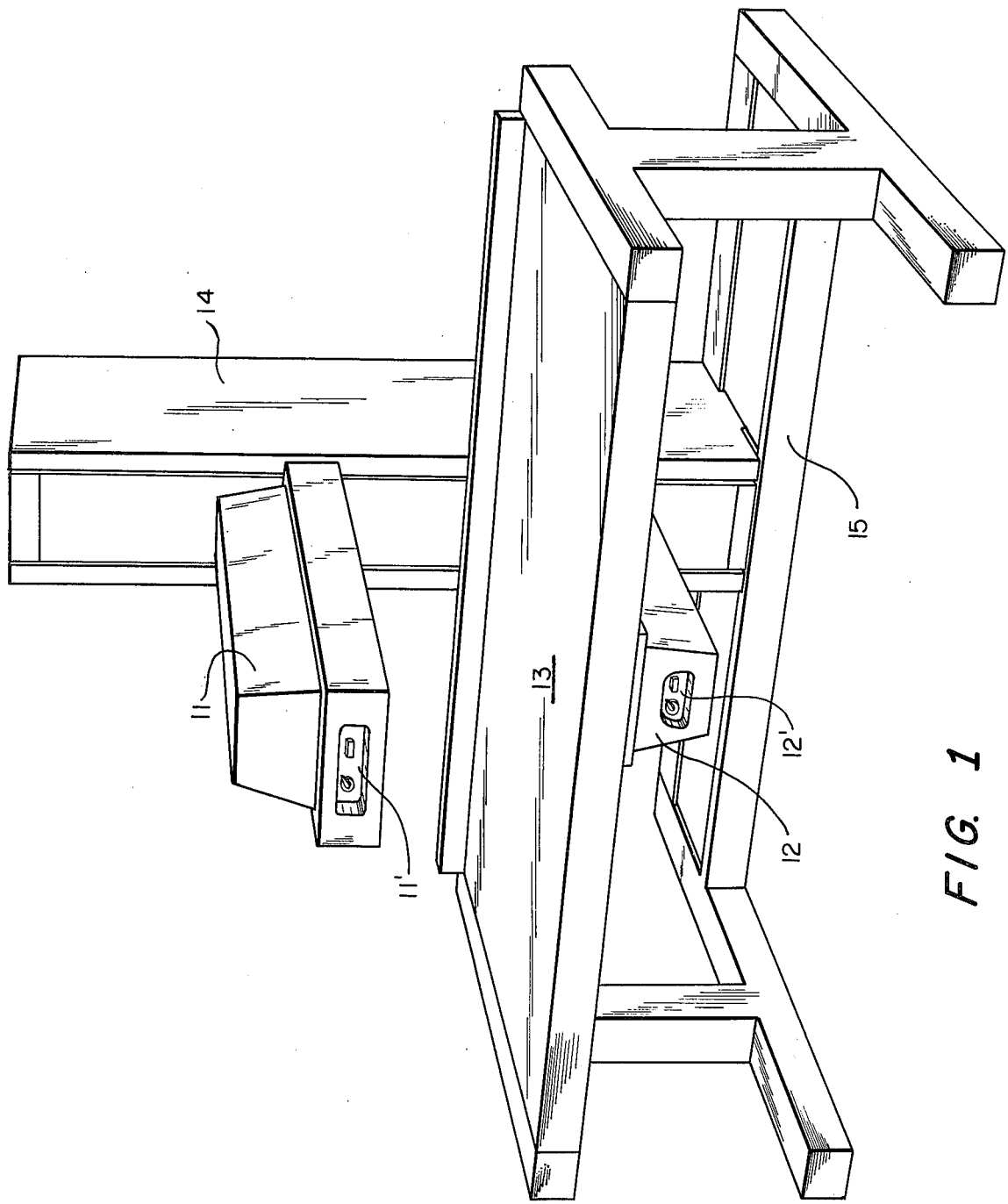
FIG. 1 is a perspective view of a patient imaging unit according to the invention.

With reference now to the drawing and more particularly FIG. 1 thereof, there is shown a perspective view of a patient imager unit according to the invention in which an upper radiation detector head assembly 11 and lower radiation detector head assembly 12 scan above and below a patient couch 13. Assemblies 11 and 12 are vertically slidable on rails carried by vertical detector head assembly support 14 which itself is slidable along rails horizontally in base support 15. Radiation detector head assemblies 11 and 12 may thus move toward and away from couch 13 carrying the patient to effectively control the height of the respective focal planes within the patient. The transverse component of the scan in each focal plane results from reciprocation of detector subassemblies within each detector head assembly. The longitudinal component of scanning occurs as vertical member 14 translates in a direction along the length of couch 13. Specific drive mechanisms for effecting the movements described above are well-known in the art and are not described in detail here to avoid obscuring the principles of the invention. Corresponding elements bear the same reference symbol throughout the drawing.

Figure 2:
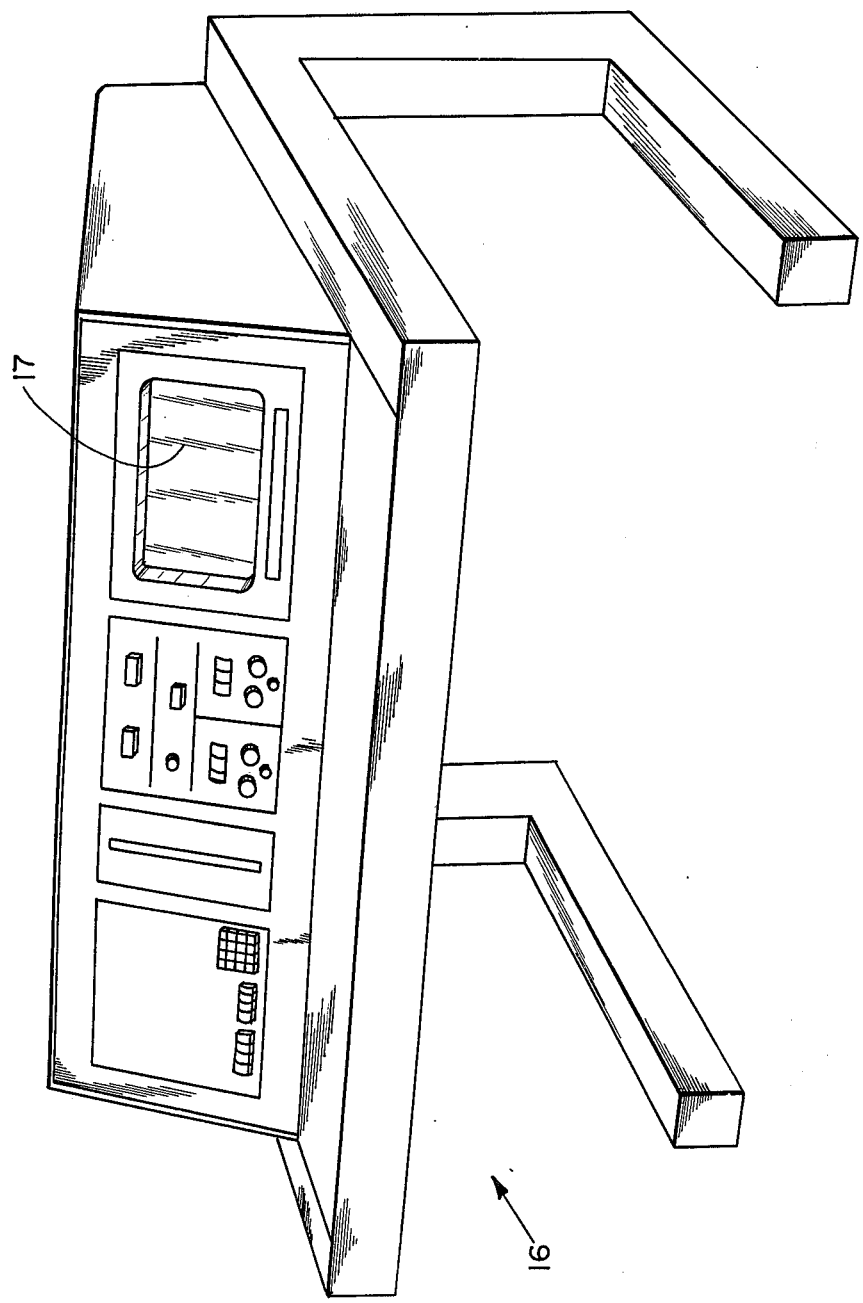
FIG. 2 is a perspective view of a suitable control console.

Referring to FIG. 2, there is shown a perspective view of an embodiment of the control console according to the invention. The control console comprises a desktype unit 16 having all the data processing and control apparatus used during image formation, including the display system for accumulating the image as it is generated and displaying it on the television screen 17 so that the operator may monitor the nature of the image being recorded. The photographic data recorder may also be housed in console 16. A floppy disc data recorder and all circuits and controls associated with recording or replay may also be located in console 16.

Figure 3:
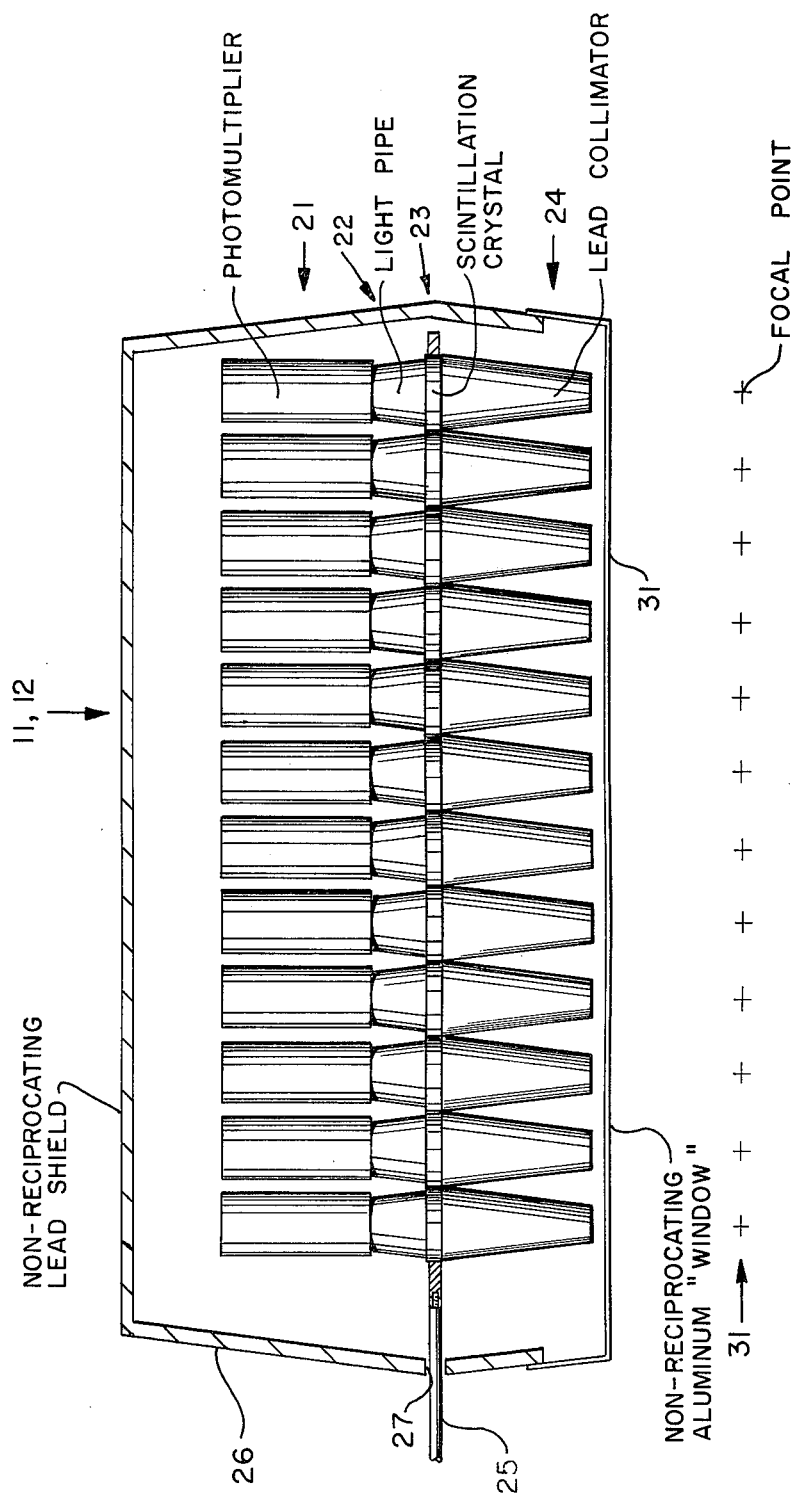
FIG. 3 is a diagrammatic representation of an imager head assembly according to the invention.

Referring to FIG. 3, there is shown a diagrammatic representation of head assemblies 11 and 12. Each of the 12 subassemblies comprises a photomultiplier 21, a light pipe 22, a scintillation crystal 23, and a lead collimator 24. A reciprocable member 25 carries all twelve detector subassemblies and enters a nonreciprocating lead shield 26 through an aperture 27. Lead shield 26 is partly open on the side facing the table, and that side is covered by a nonreciprocating aluminum window 31 through which each of the detector subassemblies receives energy from the corresponding 12 focal points 32 in the body being scanned. These focal points 32 reciprocate in synchronism as member 25 reciprocates to effectively scan the entire line segment embracing focal points 32. Each of the imaging heads 11 and 12 comprises a light-tight enclosure containing a linear array of 12 detector subassemblies each located on typically 2-inch centers. Support member 25 may be connected to a recirculating ball nut (not shown) that is caused to reciprocate by the alternative clockwise-counterclockwise action of a servo motor (not shown) turning a screw to reciprocate the entire detector assembly within the housing.

The amplitude of the reciprocating motion is preferably slightly greater than the separation between detector assemblies to permit substantially uniform velocity over the 2-inch distance between centers comprising the data-gathering part of the scan cycle. During the turn-around part of each cycle, no data is taken to avoid variations in information density. To maintain a high duty cycle the turn around time is as short as practical consistent with smooth and quiet operation, typically 0.125 seconds of a total 1.26 second scan period for a scan duty cycle of about 90%. The turn-around is preferably accomplished with a constant deceleration and acceleration of approximately 0.1g (38 inches/second$^2$) to minimize shock to the photomultiplier tubes and other components of the detector array. By keeping the lead radiation shielding 26 that prevents spurious scintillations in the crystals stationary, the weight of all the reciprocating components in a detector head assembly is only about 60 pounds, facilitating reciprocation with relatively little power. The reaction force exerted upon the supporting structure during reversal is only about 6 pounds. During the remainder of the scan cycle, the velocity is substantially uniform, preferably controlled by a tachometer-feedback rate servo, and the net reaction force on the supporting structure is then zero. Apparatus and techniques for controlling the mechanical movement described above are well-known in the art and are not described in detail here to avoid obscuring the principles of the invention.

The head assembly has a number of features. Scan velocity is low during the useful part of the cycle and turn-around may be effected quickly with minimum impulse transfer to the surrounding structure because the periodic displacement is small. By maintaining the heavy metal radiation shielding stationary, the weight of the reciprocating component is appreciably reduced to lessen the impulse transferred to the supporting structure and the power for driving the servo motor. By concealing the reciprocating components within the head housing and the structure which supports the head (the servo motor and other elements of the reciprocating drive mechanism may be supported in vertical support member 14), there is no hazard, real or psycological, associated with the reciprocating mechanism.

The invention is characterized by high quantum collection efficiently in forming images from low energy, gamma-emitting isotopes, such as technetium 99m.

The large patient format, typically 24 × 76 inches, permits single-pass whole body coverage of all but the largest adult patient while providing a high quality image that may be varied to suit different purposes by increasing image formation time (reducing scan rates) to obtain higher resolution. In a typical application for screening patients who may have bone lesions, a full format image may be obtained in 5 minutes. The image may be shown on television monitor 17 while being recorded on film and on a magnetic disc, yet is of quality comparable to that obtained in 30 to 60 minutes with conventional rectilinear scanners.

Another feature of the invention is that if the full format image discloses one or more areas of the patient requiring further study, that study may be made immediately by reimaging those areas at higher resolution. Thus, both initial screening and detailed studies may be made with the same instrument without moving the patient, and in most cases, in less than 20 minutes imaging time.

Figure 5:
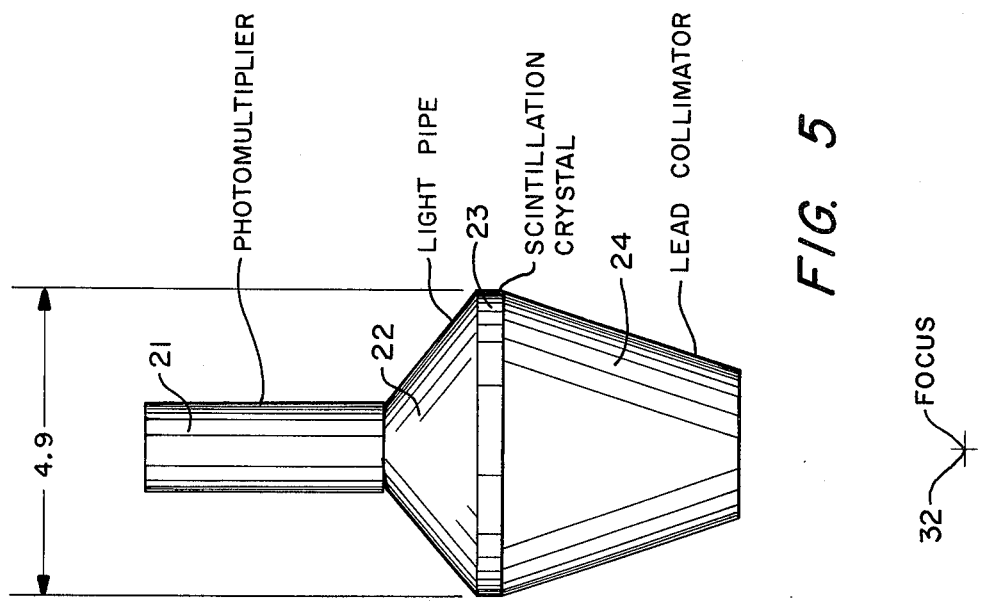
FIGS. 4 and 5 are side and end views, respectively, of a detector subassembly.
Figure 4:
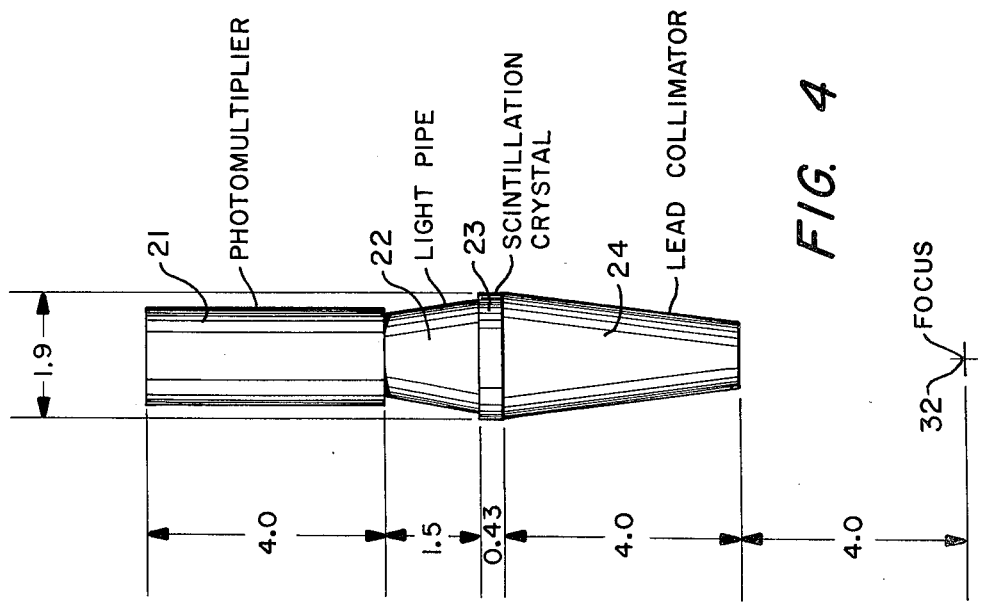

Referring to FIGS. 4 and 5, there are shown side and top views, respectively, of a typical detector subassembly with representative dimensions in inches indicated. The lead collimator 24 defines a small area around focus 32 for emitting gamma radiation collected by scintillation crystal 23. Scintillation crystal 23 converts the incident gamma radiation to corresponding optical pulses transmitted by light pipe 22 to photomultiplier 21. Photomultiplier 21 converts the incident light pulses to corresponding electrical pulses processed in a manner to be described below.

Lead collimator 24 is preferably cast from an antimony-bearing alloy of lead and contains a 5 × 13 array of tapered holes of square cross section. These tapered holes are typically 0.30 inches square on the face of the collimator that abuts the scintillation crystal 23, and about half that size at the opposite face. All of the holes are convergent so that axes intersect at a focus 4 inches from the collimator. The septa separating the holes are approximately 0.06 inches thick at the crystal face. A typical design resolution of collimator 24, defined as the full width between two points that give half amplitude for a point source of radiation, is 7.6 mm.

The scintillation crystal 23 typically comprises a thalium-activated sodium crystal mounted within a rectangular aluminum box and sealed under a window of ultra-violet transmitting glass. The bottom wall of the aluminum housing is thin, preferably less than 0.02 inches, to minimize absorption and scattering of the incident gamma rays. The side walls are approximately the same thickness to minimize the inactive area between adjacent crystals in the array.

Light pipe 22 functions as an optical funnel. The entrance face is typically a rectangle lying flat against the glass window of scintillation crystal 23. The opposite face, parallel to the entrance surface, is typically round with a diameter of 1.24 inches to match the diameter of the photomultiplier cathode. Both entrance and exit faces of light pipe 22 are preferably coated with silicone grease to minimize reflection losses at the crystal and photomultiplier inferfaces. The remaining surface is painted with white reflective paint to prevent light loss through the side of the funnel and redirect light by interval reflection. The light pipe is typically made of ultra-violet transmitting methyl methacrylate plastic. Photomultiplier 21 may be an RCA 6199, a type having a cylindrical envelope and photocathode located on the inside surface of a flat end window.

As indicated above, the invention forms the two-dimensional image of the radiant energy emission from a patient on couch 13 by a combination of reciprocal motion of the imaging head or heads transverse to the length of the patient with uniform motion of the imaging heads along the length of the patient parallel to the surface of couch 13 which supports him lying flat. FIG. 1 shows heads 11 and 12 carried by vertical support 14 over and under, respectively, the surface of couch 13. The top of couch 13 is preferably made of low density polyurethane foam sandwiched between sheets of aluminum to minimize absorption and scattering of gamma rays to the lower head 12. Heads 11 and 12 are carried on vertical rails within the support structure 14 with about 90% of the weight carried by multiple Negator springs tied to the support. Vertical adjustment of each head may be made with a proportional control located conveniently to the operator in the recesses 11' and 12' at the outboard end of each head. A drive screw may support that part of the weight not supported by the Negator spring in cooperation with a spring-loaded fail-safe brake normally in the on position and requiring electrical power for release. The brake has sufficient capacity to hold either the entire weight of the head without Negator springs or the full torque of the drive motor, singly or in combination.

The horizontal motion of the heads may be accomplished by movement of the entire vertical support structure 14 on a rail and ways on the base of the stationary structure 15. Unsightly mechanical components may be shielded from view and protected from dirt by a fabric screen which may be stored at the base of the head support structure on spring-loaded rollers which take up and pay out as the support moves.

Horizontal motion of the vertical support 14 and ends of heads 11 and 12 may be accomplished by a joystick control which may be in the recess 11' at the outboard end of upper head 11. For manual scanning the rate may be proportional to the displacement of the joystick up to a maximum speed of about 150 inches/minute. The apparatus may also include a safety-enable button which prevents either vertical or horizontal adjustment of the head position with the joystick unless the safety-enable button is depressed at the same time to avoid accidental motion by contact with the joystick. Another safety feature may comprise a contact sensor on the lower face of upper head 11 for causing all drives to stop and remain latched out when this sensor touches the patient. Those skilled in the art know how to implement these mechanical and electromechanical features just described and are not shown in detail here to avoid obscuring the principles of the invention.

Figure 6:
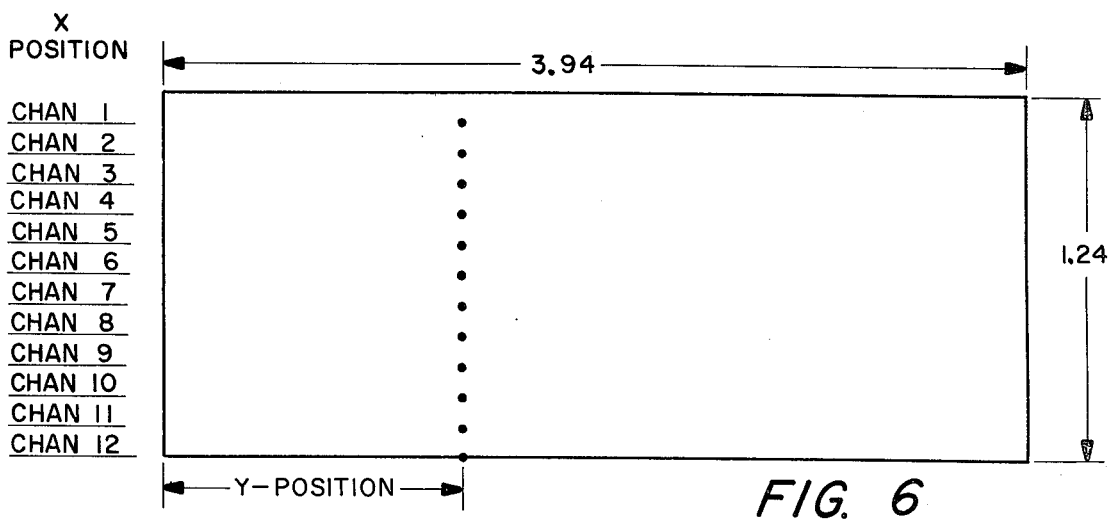
FIG. 6 is a diagrammatic representation of the display format.

Referring to FIG. 6, there is shown a suitable display format for a CRT camera display. The system generates a display raster by sequentially positioning the electron beam so that it dwells briefly at each of 12 vertical positions, designated X-position in FIG. 6, corresponding respectively to the 12 detector assemblies. This sequence repeats upon completion of the first sequence at the lower limit of each channel in the same vertical line with the display positions all raised by typically 0.0065 inches above the initial positions for the 3.94 × 1.24 display format of FIG. 6. This sequence repeats until a total of 16 sequences fill one vertical display line. The time required to complete this sequence corresponds precisely to the time required to scan the detector heads through one stroke of reciprocating motion. At the completition of the sequence the system increments the Y-position one resolution unit, and the sequence is repeated. This process of image displaying repeats until the entire format has been covered.

Figure 7:
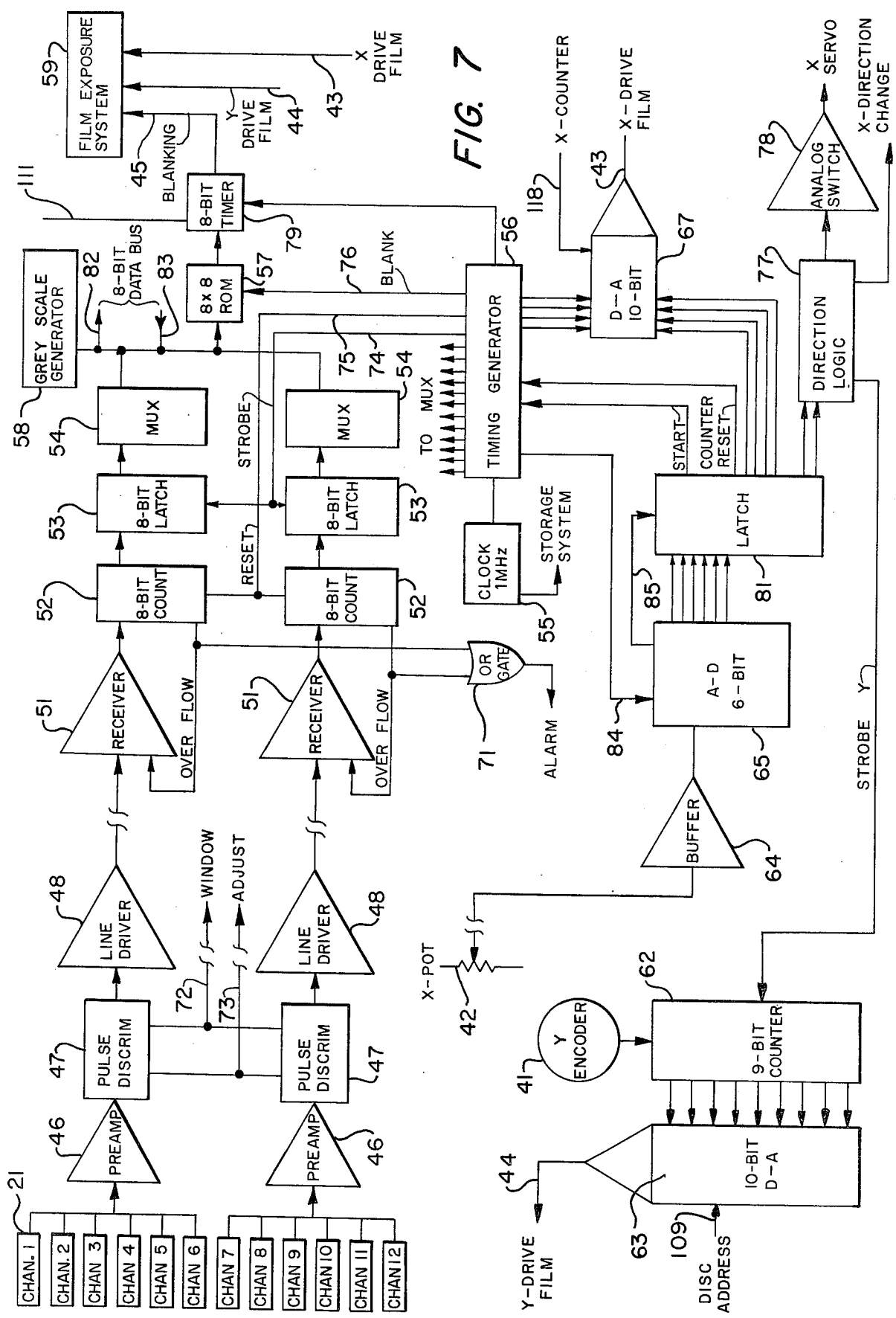
FIG. 7 is a block diagram illustrating the logical arrangement of an exemplary embodiment of the signal processor according to the invention.

Before describing in detail the CRT camera display system of FIG. 7, it is helpful to review generally the system and its mode of operation. The CRT camera display system integrates the image information gathered in the 12 separate channels to provide the wide range of exposure advantageous for maximal tonal (density) range on the image storage medium, such as photographic film. This display system uses digital-to-analog deflection circuits in both the X-direction, corresponding to the reciprocal motion of the detector array within the imaging head, and the Y-direction, corresponding to movement of the head along the body of the patient. The X-display coordinate is divided into 12 equal increments corresponding to the sub-fields of the individual detector channels, and each subfield is further divided into 1/16 resolution elements, each corresponding to a ⅛ inch lateral increment with respect to the patient.

The display system includes means for time modulating the CRT beam at each of the dwell points in the raster so that the beam is on for an interval proportional to the desired photographic exposure at that point, then turned off until it is at the next dwell point. By carefully regulating the CRT beam drive circuits, the beam-on current is a well defined constant, and the off value is below that necessary to measurably expose the film. A typical range for on times is from 18 microseconds to 1.536 milliseconds so that photographic exposure at any point in the format may be varied in steps in a range of approximately 85:1. This feature is advantageous because the final photographic image may contain a wide range of information density.

Another feature of the invention is that increasing the geometrical resolution of the display may be readily accomplished by overlapping successive displays of the X-scan by reducing the Y-increment, such as to an integral fraction of the increment which just produces a non-redundant display. This feature is especially advantageous when accumulating an image slowly to increase the resultant information density.

Referring now to FIG. 7, there is shown a block diagram illustrating the logical arrangement of an exemplary embodiment of the CRT camera display system according to the invention. The signals provided by the 12 photodetectors 21 are appropriately processed along with positional information from Y encoder 41 and X potentiometer 42 to provide X and Y drive film signals on lines 43 and 44, respectively, for application to the CRT deflection circuits to position the beam and to provide a blanking signal on line 45 to inhibit film exposure during the "X" turn around period. Each of the channels from each photomultiplier includes a preamplifier, such as 46, a pulse discriminator such as 47, a line driver such as 48, a buffer amplifier such as 51, an 8-bit counter such as 52, and 8-bit latch such as 53 and a multiplexer such as 54. FIG. 7 shows these elements only for two of the channels to avoid obscuring the principles of the invention.

A 1 mHz clock 55 provides clock pulses to the external storage system (FIG. 9) and to timing generator 56 for use in a manner to be described below. An 8 × 8 bit read-only memory (ROM) 57 receives digital signal data from multiplexers 54 or calibration signals provided by gray scale generator 58 for controlling the unblanking interval of the blanking signals provided on line 45. The Y encoder 41 may be located in base support 15 and comprise a conventional digital shaft position encoder affixed to the lead screw which provides longitudinal drive for the vertical support 14. A 9-bit counter 61, which is set to zero in one extreme position of the vertical support 14, advances when the vertical support moves away from the reference position and retards when the vertical support moves toward the reference position. Digital-to-analog converter 63 converts this count to the analog Y drive film signal provided on line 44 used for deflecting the CRT beam to an appropriate position.

X pot 42 may comprise a linear potentiometer on the detector array assembly so that the signal on the pot arm represents the instantaneous X position of the detector array. A buffer 64 couples this X signal to analog-to-digital converter 65 for transfer to latch circuit 81 which provides the least significant bits to digital-to-analog converter 67 that also receives most significant bits from timing generator 56 to provide the X drive film analog signal on line 43 for energizing the X deflection circuits that position the CRT beam in the desired X location. When the CRT is used to display data which has been recorded on the floppy disc, digital-to-analog converter 67 may also receive an X position from a disc or other random access memory over lines 118, the same memory supplying Y information to digital-to-analog converter 63.

A buffer 71 provides an alarm output signal when any of the 8-bit counters 52 provides an overflow pulse.

Having described the physical arrangement of the system, its mode of operation will be briefly discussed. The pulses representative of gamma radiation from points on the patient upon which the detectors are then focused are amplified by preamplifiers 46 and energize pulse discriminators 47. Pulse discriminators 47 also receive window adjust signals on lines 72 and 73 to control the acceptable pulse amplitude range so that only pulses within this range are coupled through line drivers 48 and buffer amplifier 51 to a respective counter 52. Each counter 52 advances in response to each acceptable pulse. Timing generator 56 provides a strobe pulse on line 74 causing each latch 53 to receive and store the count then in the associated counter 52. Immediately thereafter a reset pulse on line 75 resets each counter 52. Still later timing generator 56 provides a blank command signal on line 76 that enables 8 × 8 ROM 57 to provide 8-bit timer 79 with a digital representation when to start the unblanking signal on line 45 which ends at the completion of each cycle of timing generator 56.

Timing generator 56 provides signals on the lines designated TO MUX for enabling multiplexers 54 in sequence in the order of increasing channel number so that 8 × 8 ROM 57 converts the digital number then stored in an associated latch 53 to provide to 8 bit timer 79 a digital number representative of the interval in which the unblanking signal should be on line 45 to provide the desired exposure as discussed above. Gray scale generator 58 may also be selected in a manner to be described below.

The signal provided by Y encoder 41 advances counter 62 for each incremental displacement in a predetermined positive direction and retards the count for each displacement in a predetermined negative direction so that the count therein always represents the Y position of the imaging heads. A strobe Y signal from direction logic 77 causes digital-to-analog converter 63 to convert the count in counter 62 into an analog signal on line 44 that positions the beam at the designated Y position. The direction logic 77 is a digital comparator which provides output whenever the X-position signal reaches a value corresponding to either extreme X scan position.

Linear potentiometer 42 provides an X signal representative of the instantaneous position of the reciprocating detector subassemblies. Analog-to-digital converter 65 converts this signal to a digital signal representative of the X position for storage in latch 81 in response to strobe X signals on lines 84 and 85. Digital-to-analog converter 67 receives the four most significant bits from timing generator 56 corresponding to which of the multiplexers 54 is then enabled.

The specific embodiment of FIG. 7 is by way of example only. Those skilled in the art might perform the functions of the apparatus of FIG. 7 in many different ways. For example, digital positional encoders could be used to provide positional information in digital number form directly. Many different logical schemes might be used for converting radiation counts to unblanked duration. Alternatively, radiation counts could be converted to different pulse amplitudes of the same width or of pulses of area proportional to the count by varying both amplitude and duration.

Still another modification of the system might comprise a display rectifier for removing the bias inherent in collecting data with a moving detector. In the system of FIG. 7 the detector heads collect data for periodic display as the heads move. The physical location of each display point in the CRT format of FIG. 6 corresponds to the end (neglecting a very short delay in signal processing) of the small distance over which the data was gathered. Thus, the display point is displaced slightly in the direction of the detector motion, so that alternate lateral scans are displaced slightly in alternate directions, producing a small zig-zag in the rendition of certain image patterns.

The zig-zag pattern may be removed by alternately displacing the whole display parallel to the X-scan ½ a resolution element alternately in one direction and then the other to effectively place the display point in the middle of the area where the data was gathered so that the display point is independent of the direction of the X-scan. Rectification may be readily accomplished approximately to an acceptable practical degree by switching two unused bits of the X-drive digital-to-analog converter with the existing direction sensing logic 77. Exact correction may be readily attained by other means within the skill of those of ordinary skill in this art.

Figure 8:
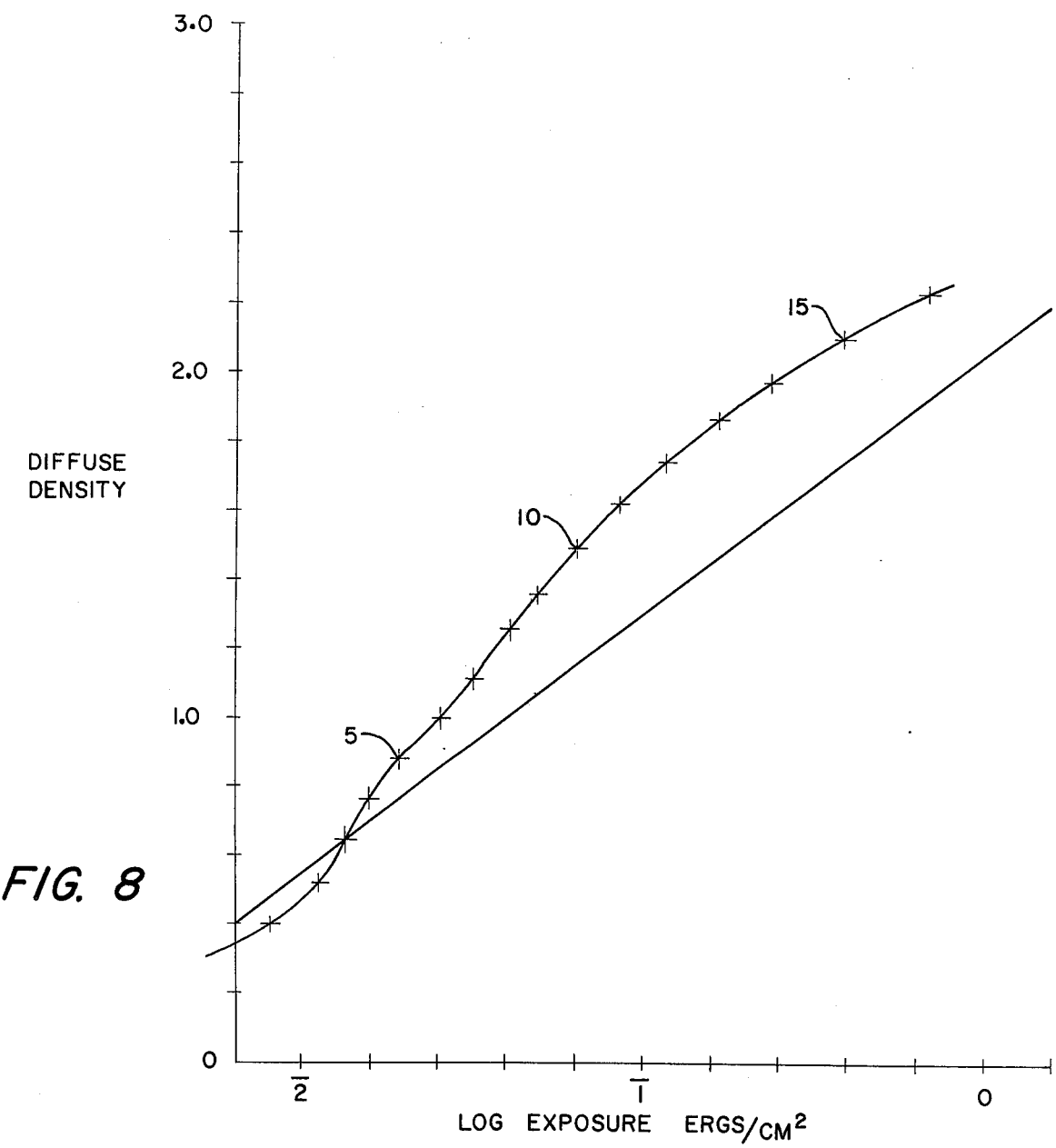
FIG. 8 is a graphical representation of the relationship between diffuse density and the logarithm of exposure for typical recording film exposed with P-11 phosphor.

Referring to FIG. 8, there is shown a graphical representation of diffuse density as a function of the logarithm of exposure in ergs/cm² for Kodak 2475 recording film exposed with P-11 phosphor with $\gamma = 1.35$ developed in D-19 developer for 12 minutes at 20° Centigrade. The gray scale generating circuit 58 functions to facilitate maximum use of the tonal range of photographic film without regard to the current-brightness characteristic of the CRT exposing the film. It is preferred to arrange the exposure so that the range of data to be recorded falls within the exposure range of the film and yet embraces as much of this range as practical to maximally use the tonal capabilities of the film. It is also advantageous to consider a characteristic of the human eye which will ultimately view the film; that is, the eye has the ability to differentiate approximately equal steps in density. Accordingly, it is advantageous to divide the whole useful range of film density from approximately 0.4 to 2.2 density units into an equal number of increments. In a specific embodiment it has been convenient to choose the number of increments as 16 that are approximately commensurate with increments that can be distinguished by the eye, each increment corresponding to 0.11 density units. For each of the density levels thus defined, an exposure value was determined for P-11 phosphor illumination, and each exposure value was converted into an on-time for a given set of beam current and camera parameters.

The table below lists the actual on time for each of the points marked on the curve in FIG. 8 and also the range of signal counts (a number proportional to information density) assigned to each level. The required exposure is obtained by programming ROM 57 in FIG. 7 in accordance with the values in the table below. The output of ROM 57 is an 8-bit parallel binary code for the time duration for each exposure for controlling timer 79 to provide the blanking signal that modulates the CRT beam.

ROM Program Table

| No. of Counts/Sample | P-11 Exposure Time-μSec |
| --- | --- |
| 0 | 11 |
| 1 | 24 |
| 2–3 | 30 |
| 4–7 | 36 |
| 8–13 | 42 |
| 14–21 | 54 |
| 22–29 | 66 |
| 30–38 | 90 |
| 39–49 | 114 |
| 50–64 | 144 |
| 65–81 | 192 |
| 82–102 | 258 |
| 103–129 | 377 |
| 130–163 | 546 |
| 164–205 | 858 |
| 206–255 | 1536 |

It may be advantageous to incorporate a gray scale generator 58 for providing known electronic signal levels for use in initial alignment of the equipment and for checking proper operation and the processing of the photographic film. The electronic reference signals for the gray scale may be in the form of 8-bit parallel binary coded signals from a diode matrix, such as a commercially available 20 × 20 diode matrix. This unit may be inserted between a multiplexer and the ROM 57 as indicated in FIG. 7. Fifteen of the available levels may be coded for signal levels corresponding to each of the ranges of signal programmed into ROM 57. The 16th level may be zero or off, and the 17th may be a direct connection from the multiplexer through to the ROM. Selection of the signal to be furnished ROM 57 may be made by inserting a diode pin at the appropriate location of the diode matrix.

In use the gray scale may be exposed on a separate photographic film apart from any radiograpahic image record, or it may be placed with a radiographic image, replacing part of the format available for radiographic information. The system of FIG. 7 shows the latter arrangement with the gray scale across the whole width of the image format as a bar of uniform density. The bars may be made any desired width by varying the length of time that the selector pin is left in each position. For most practical purposes it is sufficient to reproduce only two or three gray levels to provide an adequate check and occupy relatively little space in the display format.

An alternate method for presenting the gray scale comprises presenting the output of the diode matrix as a binary coded signal multiplexed into the ROM 57 just as if it were a 13th signal channel. In this case the gray scale would appear beside the image format without preempting any of the space allocated to the image format. It may also be advantageous to automatically switch the diode matrix levels in accordance with a predetermined program so that the gray scale appears automatically at the margin of the image format without any effort on the part of the operator.

Figure 9:
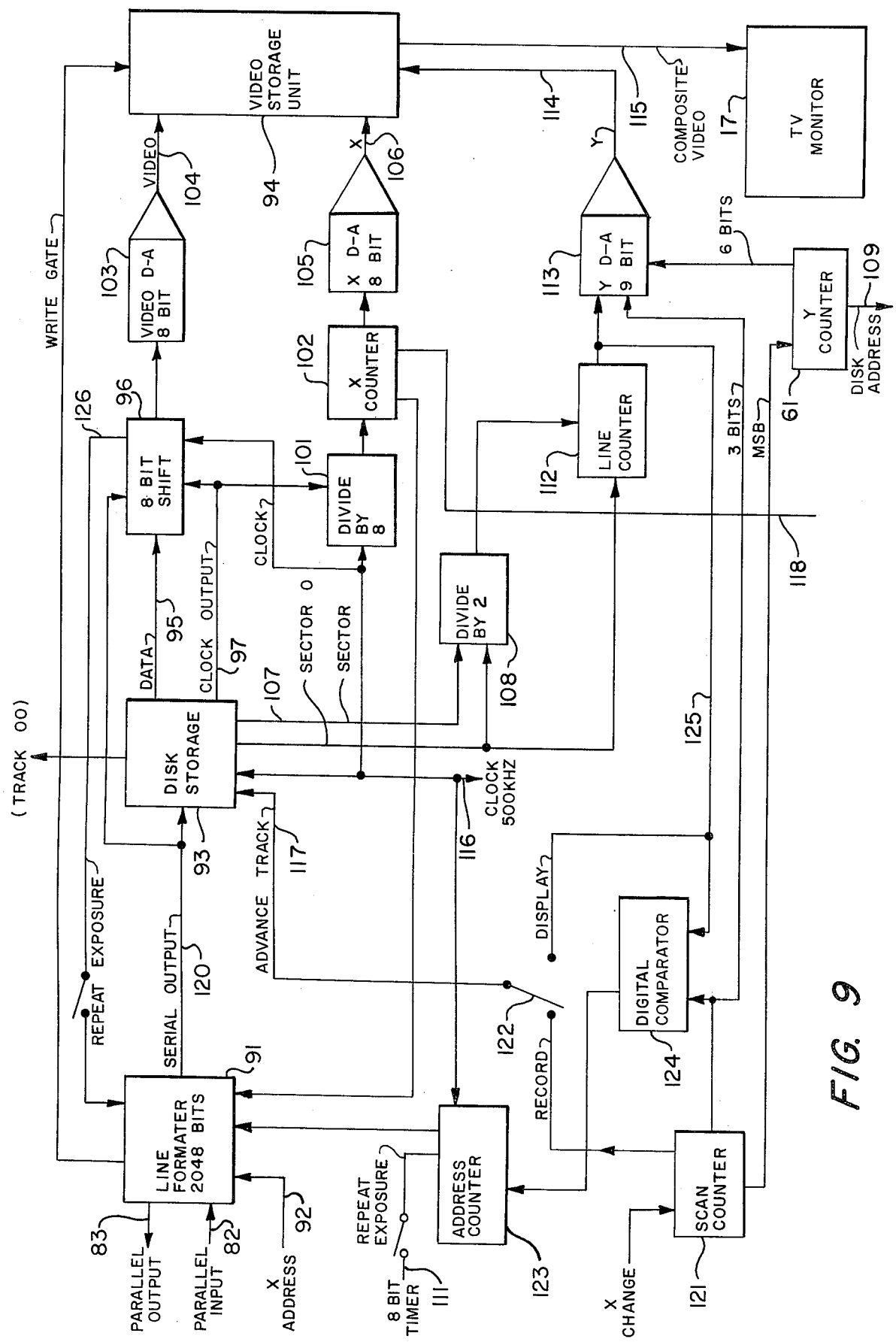
FIG. 9 is a block diagram illustrating the logical arrangement of a display system according to the invention.

Referring to FIG. 9, there is shown a block diagram illustrating the logical arrangement of a magnetic data storage system. The storage may include a line formater random access memory 91 that receives 8 parallel data bits on output line 82 for storage and transmits 8 parallel data bits on line 83 of the system of FIG. 7. RAM 91 also receives data location signals on line 92 representative of the X coordinate of the data then entering on lines 82 from latch 81 and timing generator 56(FIG. 7). This information may be stored in disc storage 93 and thereafter on TV monitor 17 after conversion to analog signals stored in video storage unit 94.

Disc storage unit 93 provides data out in serial form on line 95 to 8-bit shift register 96 which receives clock pulses on line 97 for shifting the data in and out. Divider 101 provides an output pulse to X counter 102 for each eight clock pulses to carry a count representative of the X position of the data then in 8-bit shift register 96. Video digital-to-analog converter 103 provides a signal amplitude on the video input line 104 to video storage unit 94. At the same time digital-to-analog converter 105 converts the count in X counter 102 into a representative analog signal that is applied to the X input 106 of video storage unit 94 to deflect the writing beam accordingly.

Disc storage 93 also provides a sector signal on line 107 that is divided by divider 108 to provide an output pulse on the sector 0 line to line counter 112 for advancing the latter once for every two sector pulses so that line counter 112 contains a count representative of the Y-coordinate of the video data then on line 104. Y digital-to-analog converter 113 then converts the count in line counter 112 into an analog signal that is applied to the Y-deflection input line 114 of video storage unit 94. Video storage unit 94 and TV monitor 17 exchange signals over lines 115 for displaying the image then stored in video storage unit 94 which corresponds to the image then being produced as the system scans.

Disc storage 93 receives clock pulses on line 116 from clock pulse source 55 of FIG. 7 and advance track signals on input line 117 from scan counter 121 when switch 122 is in the record position and from line counter 112 when switch 122 is in the display position. Address counter 123 also receives clock pulses from clock pulse source 55 on line 116 and starts counting when enabled by digital comparator 124 when track counter 125 and scan counter 121 bear an identity.

Having briefly described the physical arrangement of the system of FIG. 9, its mode of operation will be briefly described. RAM 91 receives a signal on lines 82 in 8-bit parallel binary form from either the multiplexing system or the gray scale generator of FIG. 7. RAM 91 reformats this signal before transmitting it in serial form. Each line of X data in the image format is assigned to one of the 64 tracks and one of the eight sectors within each track of the disc. Line counter 112 provides a measure of the position of the read-write head within the disc storage unit. Digital comparator 124 compares this count in line counter 112 with that in scan counter 121 to provide command signals whenever a change of track is required. Line counter 112 bears a count representative of the sector location then being scanned on the disc, compares this location with the X-position counter and provides a command signal for transferring the RAM data into disc storage unit 93.

Data readout may be accomplished by a similar but reverse process. The serial signal output from disc storage unit 93 on line 95 enters 8-bit shift register 96, is read out as 8-bit parallel binary and converted into a corresponding analog signal by video digital-to-analog converter 103. This data may also be transmitted on line 126 through RAM 91 and then on output lines 83 to the ROM 57 of FIG. 7.

The coordinate information associaated with the image data is carried in X counter 102 derived from the clock signal on line 97 for the X axis and in line counter 112 for the Y axis derived from the sector pulses on line 107. The signals on lines 106 and 114 shown applied to the X and Y deflection inputs of video storage input 94 may be applied to the input of digital-to-analog converters 63 and 67, respectively, in the system of FIG. 7 when it is desired to photographically record with the CRT camera display, previously stored information.

Reviewing the mode of operation of the system of FIGS. 7 and 9, the timing generator 56 provides a clock (Aprox. 650 hz on line 84). To start the analog-to-digital conversion sequence and end of conversion, a pulse on line 85 strobes latch 81, thus providing a tracking, digital output from latch 81. The start signal from latch 81 is derived from the least significant bit. This pulse represents a ⅛ inch X increment. The following sequence then takes place:

All latches 53 are updated by a pulse on line 74.

All counters 52 are reset by a pulse on line 75; counting for the next resolution element begins immediately. The 12 multiplexers 54 are sequentially interrogated by timing generator 56. The binary number that represents each channel is sent to D-A converter 67 to positon the X position of the beam in correspondence to the selected channel. The beam dwells at each of the channel positions to allow for circuit propagation delays and the time required for the 8-bit timer 79 to unblank the film exposure system (line 45). Thus, each dwell time is approx. .003 sec. A total of .036 sec is required for a 12 channel scan of the 12 multiplexers 54. The timing generator 56 then awaits for receipt of the next resolution element start from latch 81.

During each scan of multiplexers 54 the information on the data bus 82 is written into the RAM 91 whose address corrsponds to the X position in combination with the channel address. The process repeats 16 times until a full array of 192 elements corresponding to a complete line of the film and 192 8-bit words are stored in the RAM 91. The direction logic 77 will decode the end of scan and cause reversal of the scan direction thru analog switch 78.

During the turn-around time no data will be collected. This time (approx. 0.2 sec) is used to enter the 1.536 (8 × 192) bits of data from formater 91 into the magnetic disc storage 93. Starting at the first sector for the first scan the data is written serially onto the disc. The same data from the RAM 91 is transferred to 8-bit shift register 96. Clock pulses on line 116 advance address counter 123 and divide by 8 unit 101. The video D-A converter 103 generates video information to be written into electrostatic storage unit 94 via line 104. As address counter 123 is advanced, counter 102 will increment in correspondence to each resolution element stored in RAM 91. The full scan of the RAM requires approx. .008 sec. The remaining 192 ms. is used to compare the scan counter 121 with the line counter 112 thru comparator 124, causing address counter 123 to scan RAM 91 and produce serial output to disc storage 93. At the end of each turn-around period the scan counter 121 is incremented, this address enters the Y D-A converter 113 and positions the Y deflection of the video storage unit 94 and the film exposure unit D-A converter 63 via line 109.

The second scan line will proceed as above except that the "Y" counters 61 and scan counter 121 will position the Y film drive line 44 and video storage position line 114 respectively at the next line position.

This process continues until 511 lines have been scanned and stored in the 511 sectors of the floppy disc 93, video storage 94 and film exposure system 59 whereupon the whole body scan is complete.

The video storage unit 94 is switched to read during the scan and its output directed to the TV monitor 17. Thus a display of the scan is visible as it is generated since it takes only .008 seconds to write a line at the end of each scan.

Disc storage 93 generates sector pulses on line 107. These sector pulses are divided by 8 by divider 101 to create eight sectors on one track of the disc. Sector "0" resets line counter 112 and divider 108 as the disc revolves continuously. The line counter 112 output 125 is a 3-bit binary number that represents the position of the disc at any point in time. At the end of each scan, scan counter 121 is incremented. Its three least significant bits represent the sector where the data is to be recorded. Comparator 124 monitors counter 121 and line counter 112. A sync pulse is generated at the beginning of the proper sector that starts address counter 123, scanning memory 91. The contents of RAM 91 are then recorded into the disc. The serial output line 120 is also connected to the 8-bit shift register 96, bypassing the disc storage 93. Shift register 96 feeds the video D-A converter 103. This produces video signals for the storage unit 94. The output of the scan counter 121 increments Y counter 61 after eight lines have been recorded into the disc 93. The combination of three bits from scan counter 121 and six bits from Y counter 61 generate a Y position thru D-A converter 113 during the video write cycle. After eight lines of data are recorded into eight sectors of the disc 93, thereby filling a track, a track advance is generated on line 117. Data is then recorded on the next eight sectors. This sequence continues until the scan is complete.

Playback is accomplished by using data on line 95 and clock output on line 97 recorded on the disc. The disc is sequentially scanned with each sector generating a line of display data. Shift register 96 receives serial data and clock pulses from the disc storage 93 and converts it to parallel data. Every eight clock pulses provide eight bits of data representing the signal amplitude for a resolution element. D-A converter 103 converts this information to video signals to be written into video storage 94. Divider 101 increments the X counter 102 for each resolution element. X counter 102 provides the X coordinate for the video storage unit 94 thru X D-A converter 105. Line counter 112 increments one step for each sector. This information represents the Y position and is converted to the analog Y coordinate thru D-A converter 113 and sent to video storage unit 94. The process repeats until a complete frame of 511 lines by 192 elements is formed. Approximately 13 seconds is required for a complete scan of the 511 sectors on the disc.

The information read rate from disc 93 is too fast to allow proper exposure of film. To expose film from the disc, data from disc storage 93 and 8 bit shift 96 is written into the RAM 91 thru line 126. X counter 102 provides the address for RAM 91 during the write interval. One sector (line) of data is then transferred to the data bus 83 at a slower rate as required for film exposure. Address counter 123 is incremented by 8-bit timer 79 at the end of each resolution element exposure interval. X counter 102 provides X position information thru line 118 to D-A 67. After one line of data is recorded on film, Y counter 61 is incremented. This counter provides a Y coordinate thru line 109 to D-A converter 65. Upon completion of exposure for each line, a next sector is recorded into the RAM 91 from disc 93 and shift register 96, and the film exposure sequence repeats itself for the next line. The above process repeats until all 511 lines of data on disc 93 have been recorded on film. The time required for a complete exposure is 5 to 10 minutes.

The disc storage unit 93 and the gray scales may be recorded in the same manner as image information. It is also within the principles of the invention to record alphanumeric data that might be manually entered through a keyboard for identifying the patient examined, the date of the examination or any other useful information with the system capacity, typically 40 characters.

It is preferred that the X-scan cycle format include approximately 200 milliseconds of nonscanning time during the turn-around period at the end of each X-scan stroke, to permit serial readout from RAM 91 of all data accumulated during the stroke.

The magnetic data storage system of FIG. 9 may retain a permanent record of all the image information gathered during a single whole body examaination, or of one or more detailed examinations of part or parts of the body. This information may be stored on small flexible magnetic discs which may be retained as a permanent patient record in place of the usual photographic record, or in addition to photographic records. An advantage of the disc is that the patient need not be present for analysis of the image data, whether analyzed manually or with the assistance of computers. The disc may be a commercially available floppy disc comprising a small plastic disc with a magnetic coating capable of storing 2.1 million bits of data.

The display monitor 17 provides the operator with information to help insure that the desired image is being recorded either photographically or magnetically or both without having to examine the photograph or record. The display monitor may also present this information in a large enough format and with sufficient image quality so that the diagnostician may make preliminary judgment helpful in determining whether additional imaging may be desirable after the current examination. For example, a bone lesion seen in the display on a 5-minute screening examination may be clearly apparent and suggest a detailed examination of the affected area. The operator may also verify numerical data entered by keyboard. The monitor may also be used to monitor information stored on the disc.

Electrostatic storage unit 94 may typically comprise a commercially available device of this type, such as the Hughes MSC-1 scan converter which not only stores video data but also provides a conversion from the X and Y coordinates of the patient imaging unit and the CRT camera display to the conventional interlaced raster format used in commercial television.

There has been described novel apparatus and techniques for radiant energy imaging characterized by providing a relatively rapid whole image scan in a manner that efficiently utilizes system components in a reliable manner. The invention affords great flexibility in terms of the resolution available and when and in what manner the image may be analyzed. Data is available in convenient form for computer analysis. It is evident that those skilled in the art may now make numerous uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Radiant energy imaging apparatus comprising,
    patient support means for supporting a patient with the length of the patient aligned along a longitudinal direction,
    a plurality of spaced radiant energy detecting means aligned along a curve in a direction generally transverse to said longitudinal direction for providing respective signals representative of radiant energy emanating from correspondingly spaced points on a patient when on said patient support means,
    means for moving said detecting means back and forth along said curve to scan substantially the entire projection of said curve upon said patient support means,
    and means for advancing said detecting means along said longitudinal direction at a speed less than that of the speed of said detecting means along said curve to scan the entire patient.

2. Radiant energy imaging apparatus in accordance with claim 1 and further comprising means for supporting said detecting means substantially equi-distant from each other along a line substantially transverse to said longitudinal direction.

3. Radiant energy imaging apparatus in accordance with claim 1 and further comprising,
    position sensing means for providing position signals representative of the position of said detecting means,
    a cathode ray tube,
    and means responsive to the signals provided by said detecting means and said position signals for illuminating a spot on said cathode ray tube representative of a position of a respective detector with energy intensity corresponding to the radiant energy then being received by that detector.

4. Radiant energy imaging apparatus in accordance with claim 3 and further comprising means for controlling the time of said illumination in accordance with said radiation intensity.

5. Radiant energy imaging apparatus in accordance with claim 4 and further comprising,
    photographic film disposed adjacent to said cathode ray tube for being exposed by said spot to thereby record on the photographic film a visible representation of the detected radiation intensity.

6. Radiant energy imaging apparatus in accordance with claim 5 and further comprising,
    position sensing means for providing position signals representative of the position of said detecting means,
    and electrical storage means responsive to the signals provided by said detecting means and said position signals for storing information signals representative of the radiation pattern of a patient on said patient support means.

7. Radiant energy imaging apparatus in accordance with claim 1 and further comprising,
    position sensing means for providing position signals representative of the position of said detecting means,
    and electrical storage means responsive to the signals provided by said detecting means and said position signals for storing information signals representative of the radiation pattern of a patient on said patient support means.

8. A method of diagnosing a patient which method includes the steps of,
    injecting a radioactive substance into a patient,
    placing said patient upon patient support means with the length of the patient aligned along a longitudinal direction facing a plurality of spaced radiant energy detecting means aligned along a curve in a direction generally transverse to said longitudinal direction,
    moving said detecting means back and forth along said curve to scan substantially the entire projection of said curve upon said patient while also advancing said detecting means along said longitudinal direction at a speed less than that of the speed of said detecting means along said curve to scan the whole body of said patient with each detecting means scanning only a lengthwise strip of said patient different from the longitudinal strip scanned by the other detecting means while providing respective signals representative of radiant energy emanating from correspondingly spaced points embraced by said patient,
    and processing said respective signals by storing positional and intensity information to provide a map of the radiation intensity emanating from said patient.

9. Radiant energy imaging apparatus in accordance with claim 1 and further comprising,
    photographic film means responsive to film-exposing radiant energy for recording a visible representation of the amount of film-exposing radiant energy to which each point on said film has been exposed,
    a source of said film-exposing radiant energy for exposing said photographic film means,
    means responsive to the signals provided by said radiant energy detecting means for controlling the amount of film-exposing radiant energy provided by the latter source upon corresponding points on said film means whereby said film means records an image representative of the radiation emanating from the whole body of the patient being scanned, and contrast scale generating means for controlling the steps in said amount of film-exposing radiant energy for better utilizing the available tonal capabilities of said photographic film means.

10. Radiant energy imaging apparatus in accordance with claim 9 wherein said contrast scale generating means includes means for establishing said steps to correspond to increments in tonal gradations substantially equally discernible by the human eye.

* * * * *